United States Patent [19]
Vokhmin

[11] Patent Number: 6,075,591
[45] Date of Patent: Jun. 13, 2000

[54] OPTICAL METHOD AND APPARATUS FOR DETECTING LOW FREQUENCY DEFECTS

[75] Inventor: Peter A. Vokhmin, Ariel, Israel

[73] Assignee: Prolaser Ltd., Rosh Ha'Ayin, Israel

[21] Appl. No.: 08/967,305

[22] Filed: Oct. 21, 1997

[30] Foreign Application Priority Data

Dec. 17, 1996 [IL] Israel ......................................... 119850

[51] Int. Cl.[7] .................................................. G01N 21/00
[52] U.S. Cl. ..................................... 356/239.1; 356/239.2
[58] Field of Search ................................. 356/371, 445, 356/430, 446, 237.1, 239.1, 239.2, 239.7; 250/550, 562, 563, 572, 571, 559.12

[56] References Cited

U.S. PATENT DOCUMENTS

| 3,743,431 | 7/1973 | Cushing et al. | 356/239 |
|---|---|---|---|
| 3,892,494 | 7/1975 | Baker et al. | 356/239 |
| 4,459,027 | 7/1984 | Kafri et al. | 356/376 |
| 4,547,073 | 10/1985 | Kugimiya | 356/371 |
| 4,810,895 | 3/1989 | Kafri et al. | 250/571 |
| 5,016,099 | 5/1991 | Bongardt et al. | 358/106 |
| 5,309,222 | 5/1994 | Kamei et al. | 356/371 |

FOREIGN PATENT DOCUMENTS

| 0152894 | 8/1985 | European Pat. Off. . |
|---|---|---|
| 0372241 | 6/1990 | European Pat. Off. . |
| 3926349 | 2/1991 | European Pat. Off. . |
| 3237511 | 4/1984 | Germany . |

*Primary Examiner*—Robert Kim
*Assistant Examiner*—Michael P. Stafira
*Attorney, Agent, or Firm*—Browdy and Neimark

[57] ABSTRACT

Inspection of an optical object for the existence therein of inhomogeneities, comprises providing a diverging beam of inspection radiation and directing the beam on the optical object so that each point thereof is illuminated at a single angle; projecting the beam through the optical object on a projection screen and obtaining thereby a shadow pattern thereof, the optical inhomogeneities being distinguishable in the shadow pattern owing to the difference in the brightness of the areas corresponding thereto over the background brightness of the pattern; imaging the shadow pattern via the optical object in such a manner that the rays forming the image pass through each point of the optical object at an angle corresponding to the angle at which the point is illuminated; and detecting and analyzing the image of the shadow pattern.

20 Claims, 10 Drawing Sheets

OPTICAL METHOD AND APPARATUS FOR DETECTING LOW FREQUENCY DEFECTS

FIELD OF THE INVENTION

The present invention refers to the optical inspection and, particularly, to the automatic optical inspection of optical objects for defects and/or inhomogeneities which cause variations of their local optical properties.

BACKGROUND OF THE INVENTION

One type of the above specified methods is based on phase interferometry and moire principles in accordance with which an optical object is inspected by the detection and analysis of interference and moire patterns created by the interaction of inspection radiation which passes through the optical object with reference radiation or a grating. Examples of methods of this type are disclosed, for example, in U.S. Pat. No. 4,459,027 and U.S. Pat. No. 4,810,895. However, these methods suffer from low resolution and require complicated interpretation of the produced images, which renders these methods inefficient, slow and expensive.

U.S. Pat. No. 5,309,222 and DE 3 237 511 disclose methods of another type, in which optical objects to be inspected are placed on an optical path of a television camera and are used to display a test pattern on the camera. A video signal obtained thereby is compared with a control signal not influenced by the inspected object and, based on a deviation therebetween, flaws in the inspected object are identified. However, methods of this type are suitable only for the inspection of flat objects. In addition, they are not capable of the detection of small flaws.

There also exist well known "shlieren" photography and "shadowgraphy" inspection methods which are based on the analysis of a shadow picture obtained as a result of phase changes in inspection radiation beams passing through or reflected from inspected optical objects. However, since in such an analysis the shadow picture depends on the optical power of inspected objects, it is extremely difficult and often almost impossible to use this analysis in automated quality control where pictures obtained from different inspected objects must be captured by one pre-set imaging device. In addition, the known methods of analysis of phase objects cannot determine accurately actual dimensions and locations of the object's flaws.

SUMMARY OF THE INVENTION

It is the object of the present invention to provide a new method and apparatus for the inspection of optical objects for optical inhomogeneities, in which the disadvantages of the above prior art are substantially reduced or overcome.

In accordance with one aspect of the present invention, there is provided a method for the inspection of an optical object for the existence therein of inhomogeneities, said method comprising providing a diverging beam of inspection radiation and directing said beam on said optical object so that each point thereof is illuminated at a single angle;

projecting said beam through said optical object on a projection screen and obtaining thereby a shadow pattern thereof, said optical inhomogeneities being distinguishable in said shadow pattern owing to the difference in the brightness of the areas corresponding thereto over the background brightness of the pattern;

imaging said shadow pattern via said optical object in such a manner that the rays forming said image pass through each point of the optical object at an angle corresponding to said angle at which said point is illuminated; and detecting and analyzing said image of the shadow pattern.

In accordance with another aspect of the present invention, there is provided an apparatus for the inspection of an optical object for the existence therein of inhomogeneities comprising:

illumination means for providing a diverging beam of inspection radiation and for the illumination of said optical object thereby so that each point thereof is illuminated at a single angle of the incident radiation, and providing, by means of said optical object, a shadow pattern thereof on a projection screen;

imaging means for imaging said shadow pattern via said optical object in such a manner that the rays forming said image pass through each point of the optical object at an angle corresponding to said angle at which said point is illuminated; and image detecting means and image processing means for analyzing said image of the shadow pattern for said inhomogeneities.

Preferably, the exit pupil of the illumination means and an entrance pupil of said imaging means are optically equidistant from the inspected optical object.

The main idea of the present invention is to ensure that the imaging rays which form the image of the shadow pattern of the optical object, propagate along the same optical path as the incident rays illuminating the optical object, i.e. the illuminating and imaging branches of the inspection system are brought into optical coincidence. The consequence of such an arrangement is that the shadow pattern which depends on the optical power of the optical object is imaged at a power-independent geometrical scale. Thereby, shadow patterns of different objects may be captured by one pre-set imaging device, which renders the method and the apparatus of the present invention particularly suitable for automated quality control.

Preferably, the image detecting means is in the form of a multi-element detector capable of measuring the brightness distribution in the image of the shadow pattern.

Preferably, the illumination means is a point source of radiation, the projecting screen is a high resolution back-scattering surface and the imaging and detecting means is a high resolution TV camera.

Depending on the type of the inspected optical object, the apparatus according to the present invention may comprise means for the correction of the form of the shadow pattern.

The method and apparatus according to the present invention may be used for the inspection of both transparent phase objects and specular objects having at least one reflecting surface. Both the transparent and the specular objects may have curved and flat shapes and may be in the form of optical elements or rather in the form of a sheet material translated linearly and transversely to the direction of the radiation propagation. The method and the apparatus of the present invention may be used not only for the inspection of optical objects but also for their mapping based on the local measurements of the optical power of the objects.

BRIEF DESCRIPTION OF THE DRAWINGS

For a better understanding of the present invention and to show how the same may be. carried out in practice, reference will now be made to the accompanying drawings, in which

FIG. 1b illustrates an electrical response to an optical signal obtained by the imaging and detection of the shadow pattern shown in FIG. 1a;

DESCRIPTION OF THE PREFERRED EMBODIMENT

Figure 1:
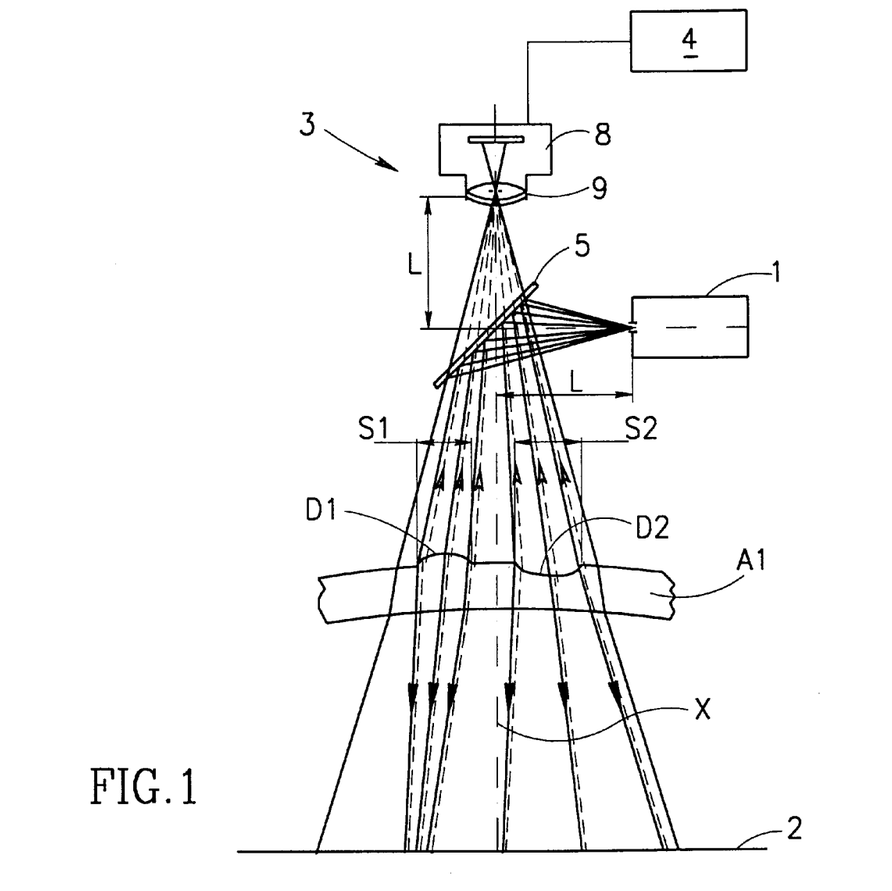
FIG. 1 is a schematic illustration of a principal embodiment of an apparatus according to the present invention.

FIG. 1 schematically illustrates a principal embodiment of an apparatus for optical inspection of an optical object A1 (only a portion of which is shown) for the existence of inhomogeneities and/or defects in its bulk or on its surfaces, such as for example defects D1 and D2. For the purpose of illustration, the inspected portion of the optical object A1 and the defects D1 and D2 are shown substantially exaggerated.

As seen, the apparatus comprises illumination means 1 for the illumination of the optical object A1 with a diverging incident radiation beam, a projecting screen 2 on which the optical object A1 projects the incident radiation beam, imaging and detecting means 3 for the observation of the projected radiation and the detection thereof, and image processing means 4 for the analysis of the image. The apparatus also comprises a beam deflecting element 5 which directs the incident beam towards the inspected object A1 and which passes the imaging rays towards the imaging means 4.

The illumination means 1 is in the form of a point source of radiation of any design providing suitable, preferably wide, divergence of radiation illuminating the optical object A1 along an optical axis X. It is desirable that the point source of radiation has minimal possible dimensions, whereby high resolution of measurements may be obtained and the inhomogeneities or defects distinguishable thereby may be very small.

The beam deflecting element 5 is, preferably, a beamsplitter of any suitable type. Thus, the beam deflecting element 5 may be in the form of an ordinary beam splitting mirror or it may rather be designed as a polarizing beamsplitter followed by a $\lambda/4$ retarding plate. The beam deflecting element 5 may also be in the form of a color separating dichroic mirror.

The projecting screen 2 may be in the form of a diffusing or luminescent or phosphorescent surface or rather any kind of back-scattering surface such as, for example, described in G. W. Neudeck et al, Precision crystal corner cube arrays for optical grating formed by (100) silicon planes with selective epitaxial growth, App. Opt. 35, 3466–3470, 1996.

The imaging and detecting means 3 of the apparatus 1 is in the form of a TV camera 8, such as for example CCD, with an imaging lens 9 having a large depth of focus. The camera 8 is disposed on the optical axis X so that a pupil of the lens 9 is spaced from the beam deflecting element 5 at a distance L equal to the distance between the point source of radiation 1 and the beam deflecting element 5. Thereby, the TV camera is brought into the optical coincidence with the point source of radiation, i.e. they are optically equidistant from the optical object A1.

It is desirable that the TV camera has a high resolution. In general, the resolution of measurements in accordance with the method of the present invention is determined as follows:

$$\delta = \sqrt{\left(\frac{a \cdot B}{B + A}\right)^2 + \left(1.22 \cdot \lambda \cdot \frac{A}{d}\right)^2 + c^2}$$

where a defines dimensions of the point source of radiation, c is the resolution of the TV camera, d is a diameter of the pupil of the TV camera lens, A is a distance from the source of radiation (and the lens of the camera) to the inspected optical object, B is a distance from the inspected optical object to the projecting screen, $\lambda$ is the wavelength of the illuminating radiation.

The image processing means 4 comprises a computer to which the image is transferred via a frame grabber and which is provided with a dedicated software for the analysis of the defects, including the determination of their location, dimensions and types (waviness, orange peel, striae, etc). Monitoring and analyzing systems associated with the computer may be of any suitable type.

Figure 1A:
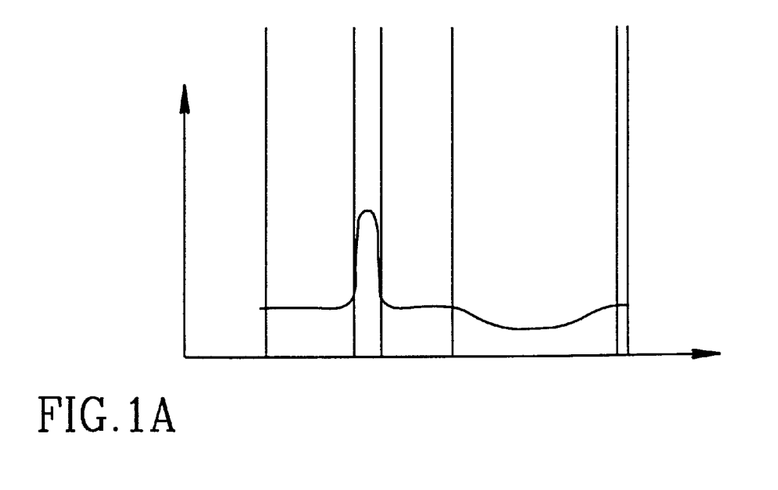
FIG. 1a illustrates the distribution of brightness in a shadow pattern of an optical object A inspected by the apparatus shown in FIG. 1.

In operation, the optical object A1 illuminated by the incident radiation, forms on the projecting screen 2 a shadow pattern in the form of the distribution of brightness which, as shown in FIG. 1a, depends on the optical power of the optical object A1 and on the local deviations thereof introduced by the defects D1 and D2. Thus, as seen, the defects D1 and D2 cause the difference in brightness of the areas corresponding thereto over the background brightness of the pattern.

Figure 1B:
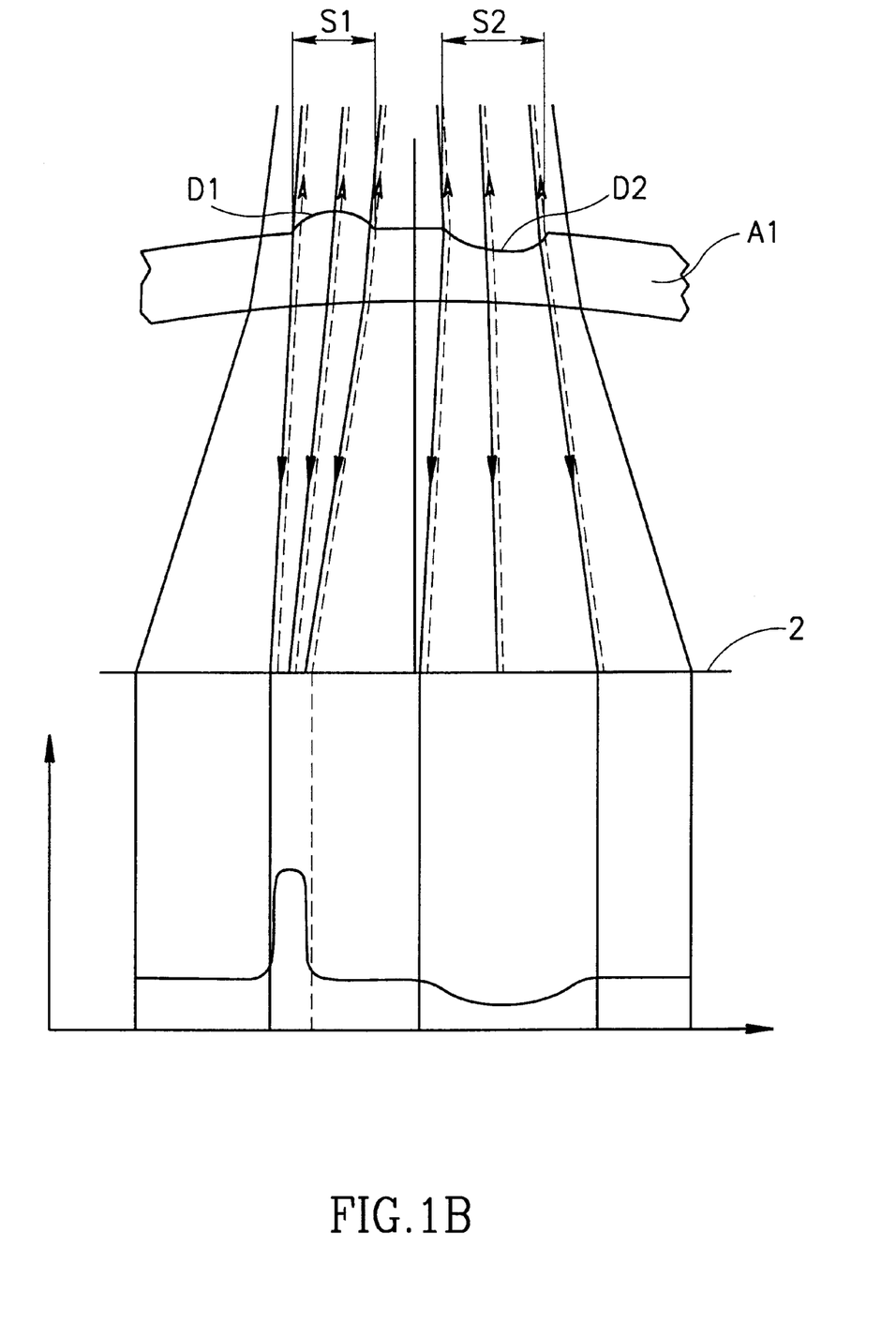

The TV camera 4 images the shadow pattern via the optical object A1. Since the TV camera 4 is in the optical coincidence with the point source of radiation 1, the rays forming the image propagate along the same optical path as the incident rays illuminating the optical object. Therefore, in the image of the shadow pattern, relative dimensions S1 and S2 of the defects D1 and D2 and their mutual disposition are not distorted but are rather exactly the same as in the shadow pattern. This is illustrated in FIG. 1b which shows a response of the TV camera to the optical signal obtained from the image of the shadow pattern. This response may be generally described by the following expressions:

$$S = P \cdot Const \cdot \frac{Fs^2}{(Fs \cdot (A + B) - A \cdot B)^2}$$

for optical objects with spherical power Fs; and $$S = P \cdot Const \cdot \frac{Fc}{(Fc \cdot (A + B) - A \cdot B) \cdot (A + B)}$$

for optical objects with cylindrical power Fc.

FIGS. 2 to 6 illustrate different embodiments of the apparatus of the present invention.

Figure 2:
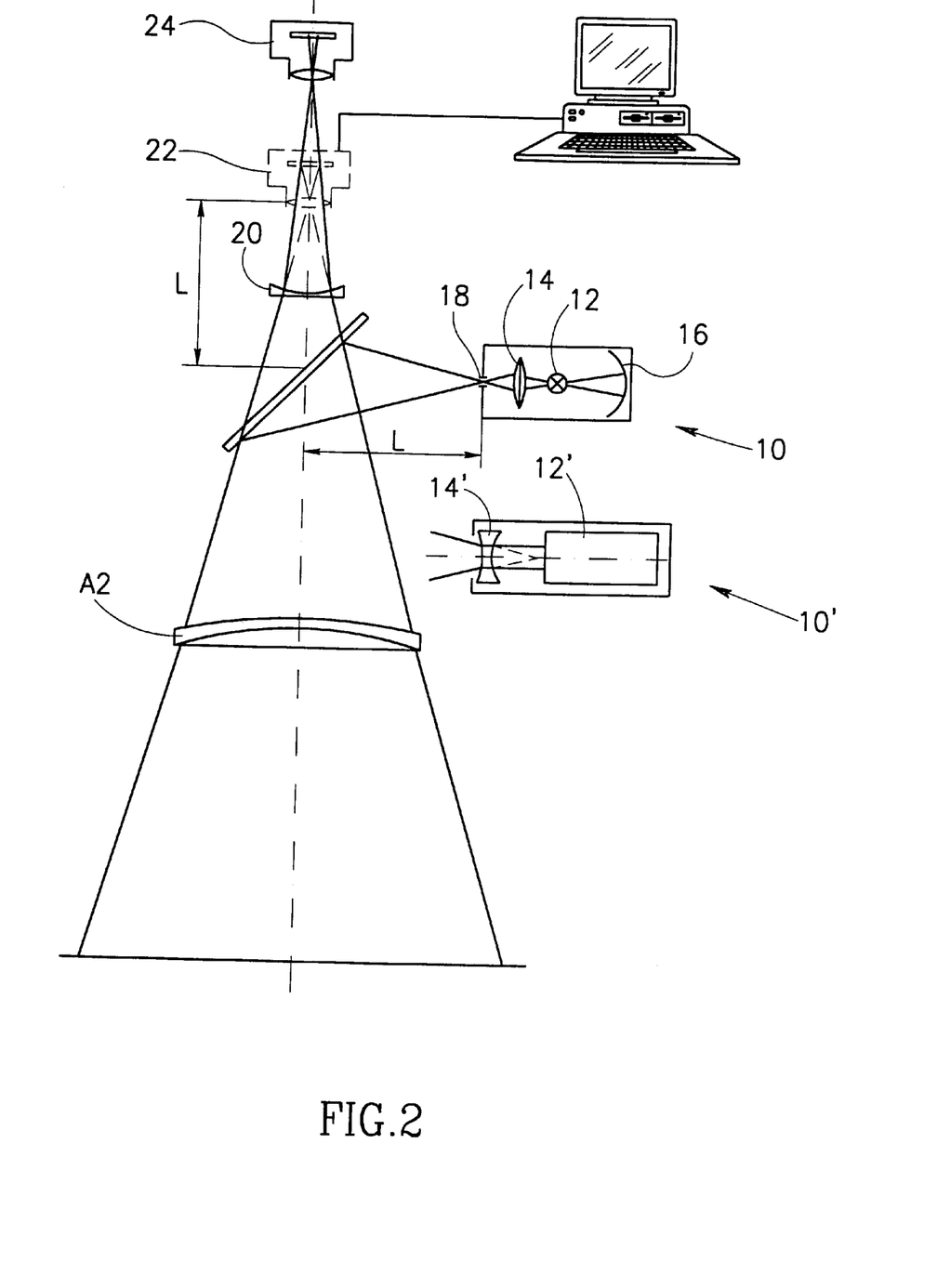
FIGS. 2, 3, 4, 5 and 6 illustrate different embodiments of the apparatus shown in FIG. 1.

An apparatus according to the embodiment of FIG. 2 has the illumination means in the form of a unit 10 consisting of a source of radiation 12 which may be an arc or filament halogen lamp, a focussing optics 14, a concave mirror 16 and a pinhole 18 which in fact represents a point-like exit of the source of radiation 10. As seen, an alternative design of the unit 10, is a unit 10' comprising a laser 12' followed by a focussing or defocussing optics such as, for example, a negative lens 14'. FIG. 2 also illustrates the configuration in which an element 20 is used in the imaging branch of the apparatus, to bring the image 22 of a camera 24 into the optical coincidence with the unit 10. If required, a similar element may be used in the illumination branch of the apparatus.

Figure 3:
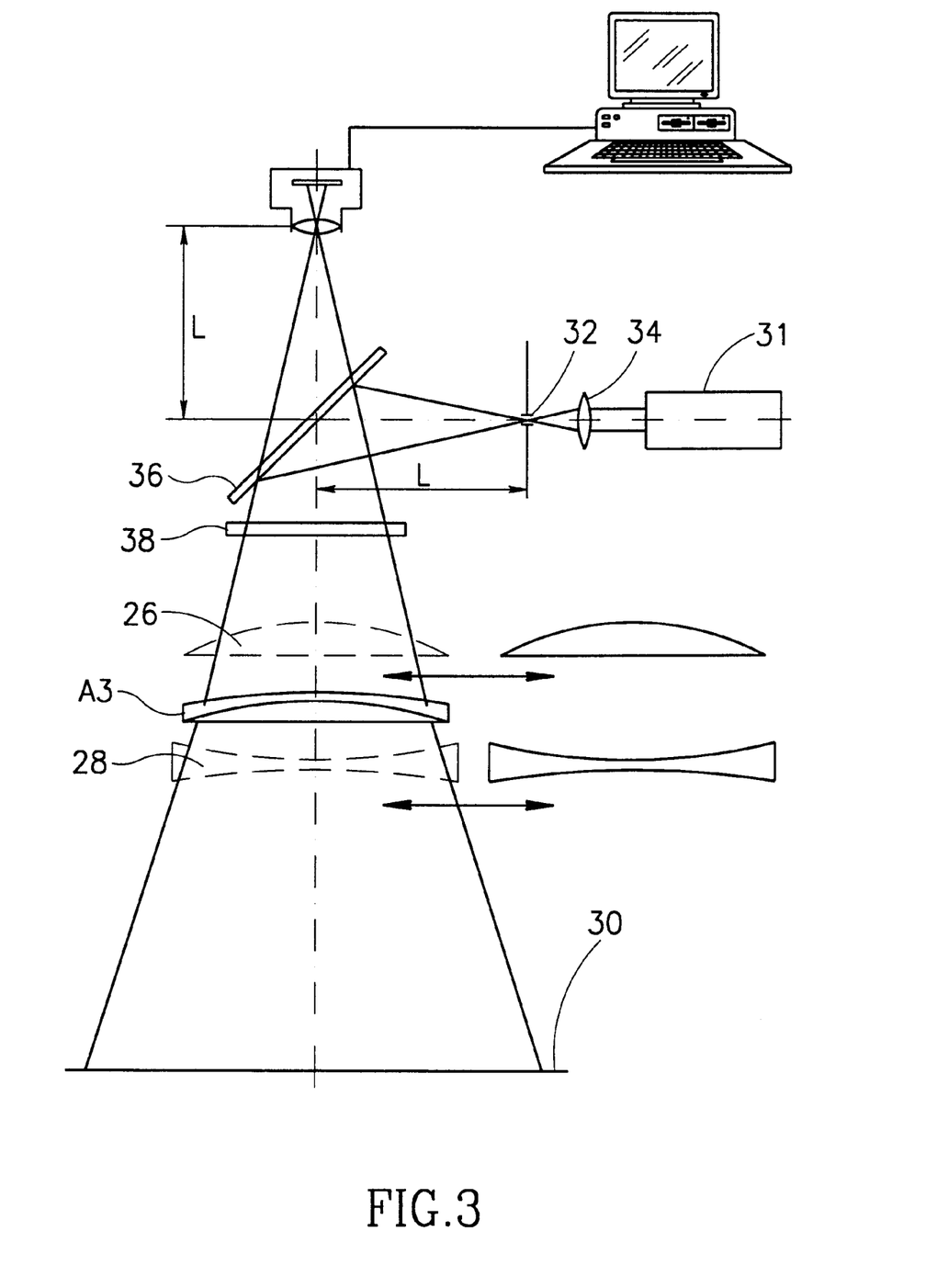

FIG. 3 illustrates an apparatus of the present invention specifically suitable for the inspection of high power optical objects. In order to compensate this high power, the apparatus of FIG. 3 may use one of two removable lenses 26 and 28 which bring the radiation incident on an optical object A3 and on a projecting screen 30 to suitable divergence. Thus, when the inspected optical object A3 is a high power negative lens, the removable lens 26, preferably designed as a positive meniscus lens, is to be used to reduce the divergence of the illuminating radiation beam and to compensate thereby its excessive divergence after the beam passes through the optical object A3. When, however, the inspected optical object A3 is a high power positive lens, the removable lens 28, preferably designed as a negative meniscus lens, is to be used to additionally diverge the radiation beam and to avoid the focussing thereof in front of the projecting screen 30.

In the apparatus of FIG. 3, the illumination means is in the form of a laser 31 producing a collimated radiation beam which illuminates a pinhole 32 through a focussing lens 34. The beam deflecting element of the apparatus is in the form of a polarizing beam-splitter 36 followed by a $\lambda/4$ retarding plate 38.

Figure 4:
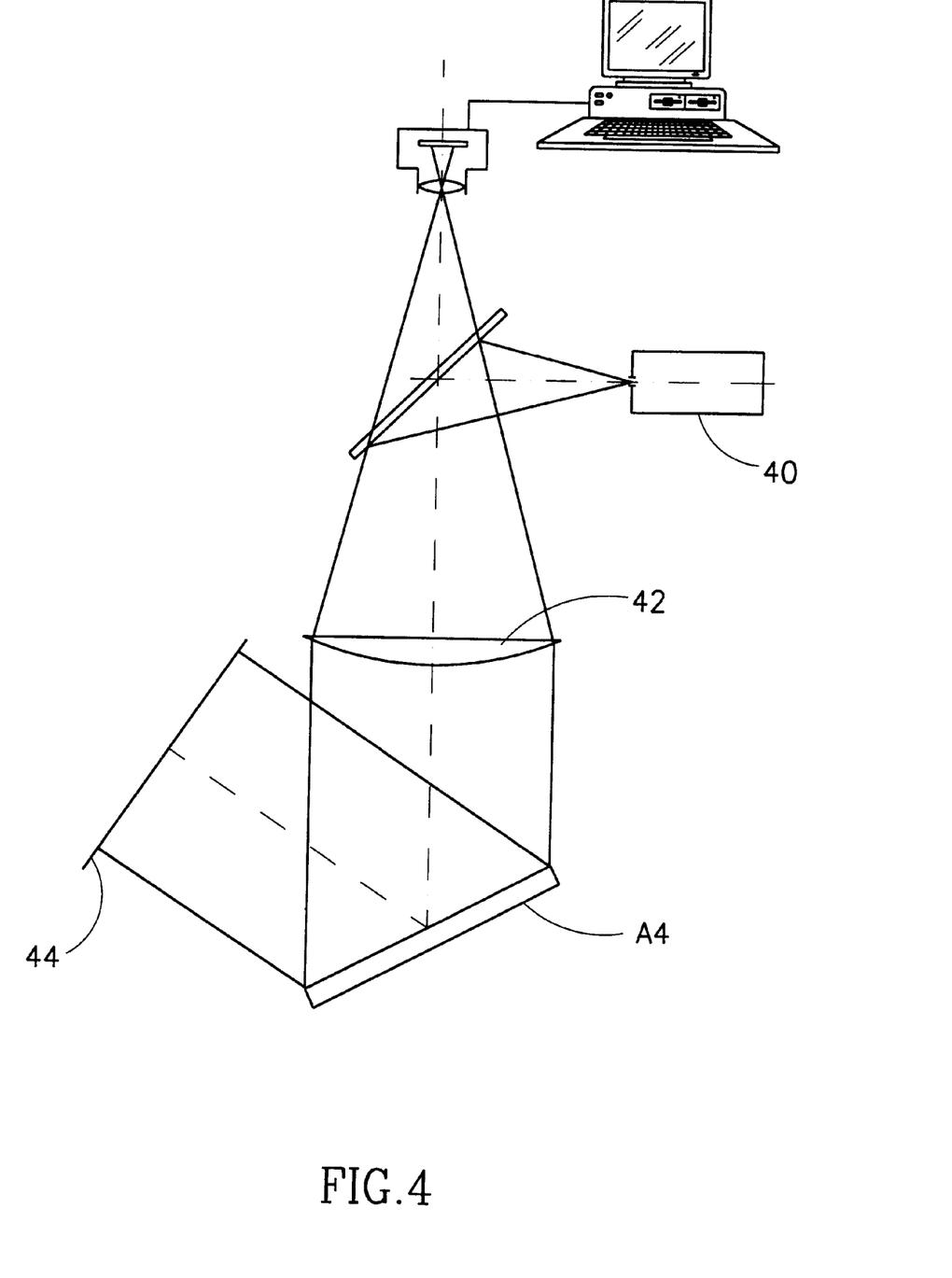

FIG. 4 illustrates an apparatus according to the present invention, designed for the inspection of specular objects. The illumination means of the apparatus of FIG. 4, comprise a point source of radiation 40 providing a diverging illuminating beam and a positive lens 42 which transforms the diverging beam into a collimated beam for the illumination of an inspected optical object A4 having a reflective surface and producing a shadow pattern thereof on a projecting screen 44.

Figure 5:
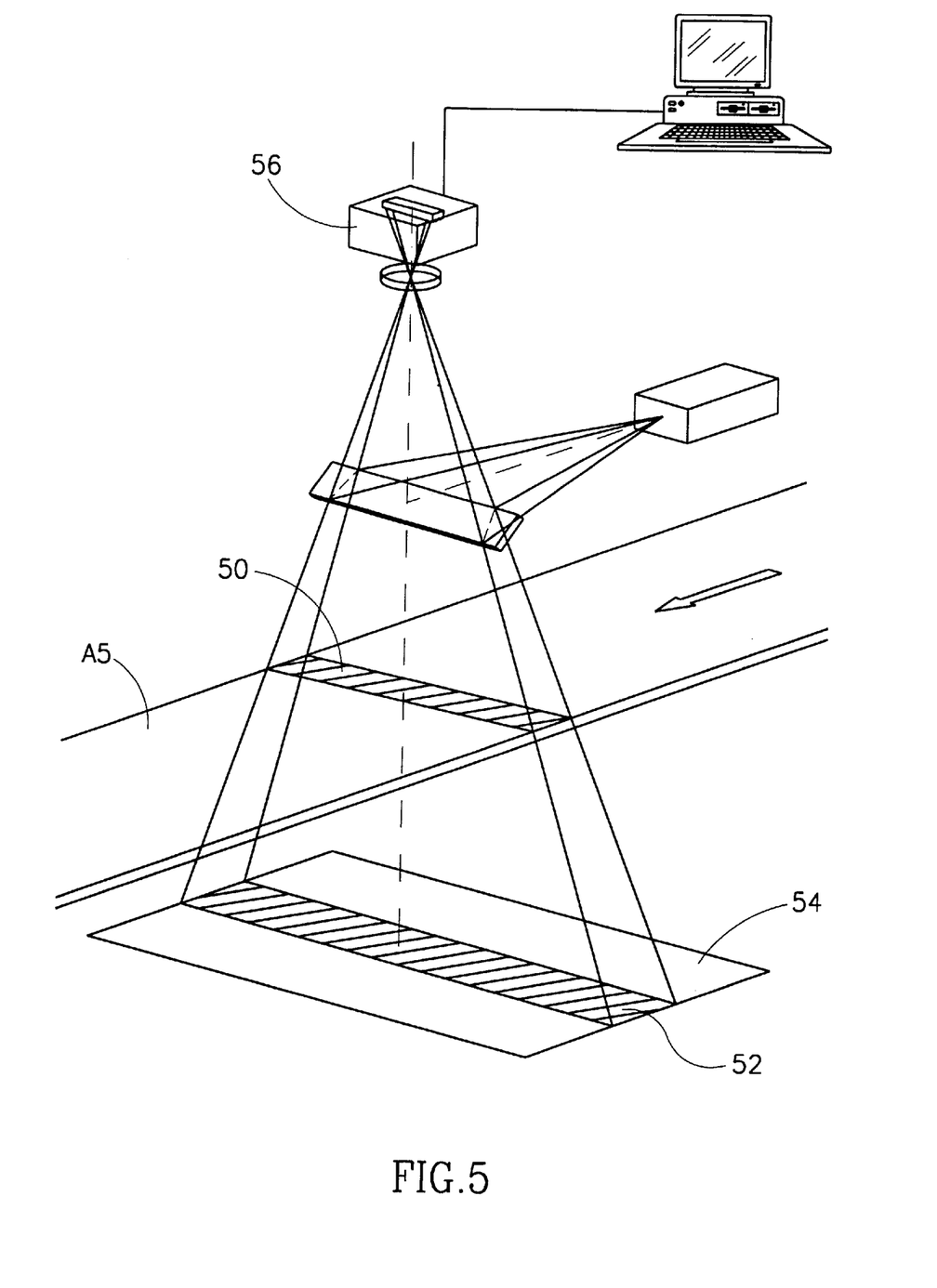

FIG. 5 illustrates an apparatus according to the present invention, designed for the inspection of a linearly translated transparent sheet material A5. In this case, the inspected material A5 is illuminated by a transversely diverging light beam forming a stripe 50 of light on the inspected surface of the material. The material A5 is scanned stripe by stripe and the image of the shadow pattern 52 obtained on a projecting screen 54, is detected by a multi-element line scan detector 56.

Figure 6:
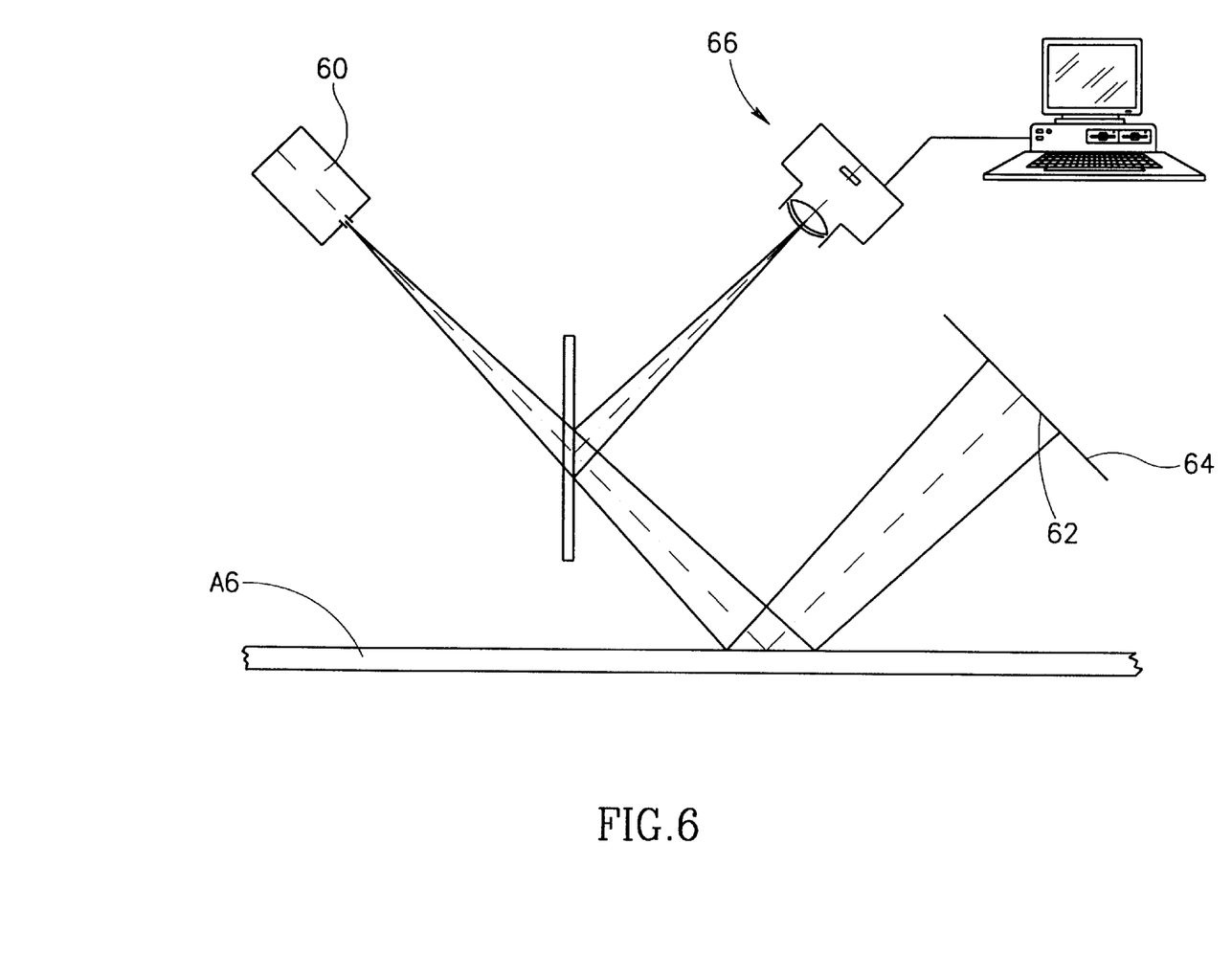

FIG. 6 illustrates an apparatus according to the present invention, designed for the inspection of a linearly translated specular sheet material A6. This embodiment is similar to the embodiment of FIG. 5 in that the inspected object A6 is illuminated by a stripe of light from a source of radiation 60 and in that the image of a shadow pattern 62 produced thereby on a projecting screen 64, is detected by a multi-element line scan detector 66.

Figure 7A:
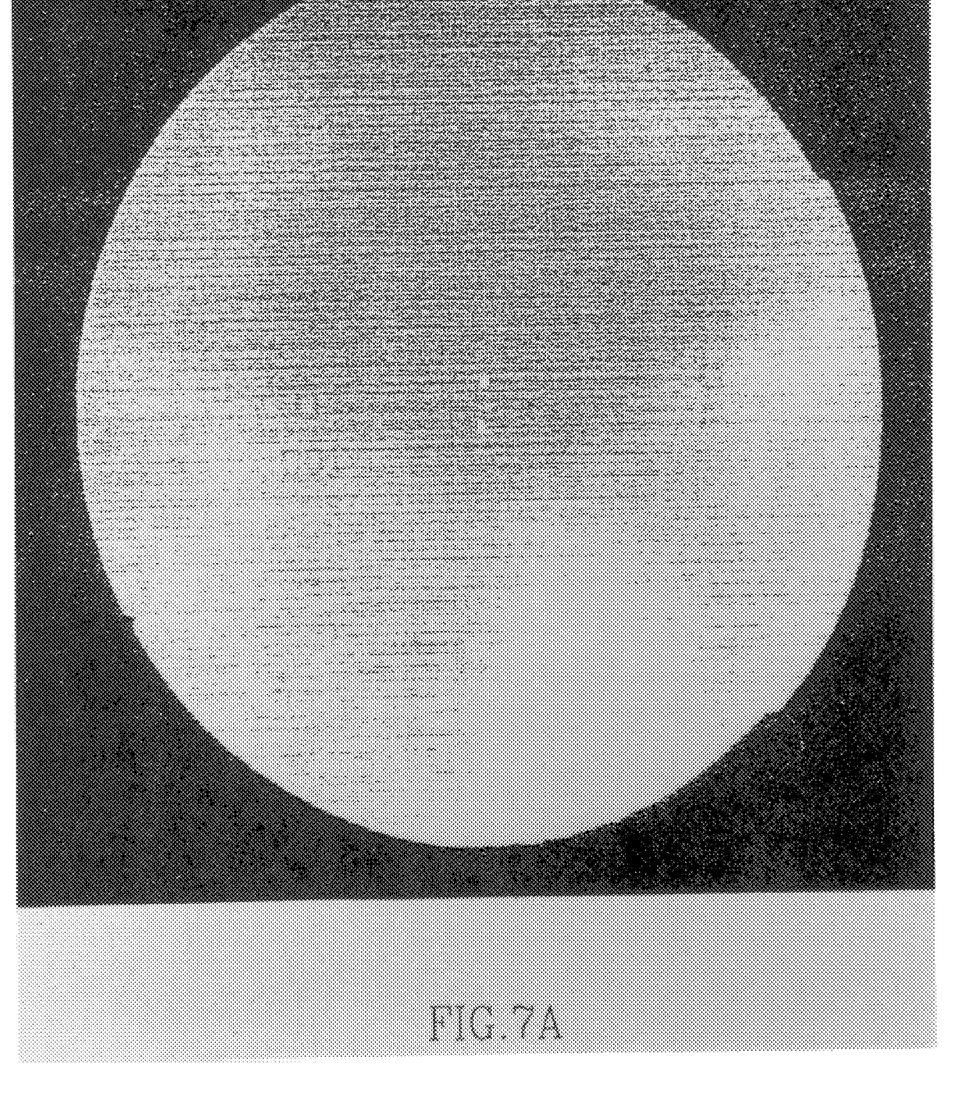
FIGS. 7a and 7b illustrate images of shadow patterns of a progressive lens obtained, respectively, in accordance with the present invention and conventionally.
Figure 7B:
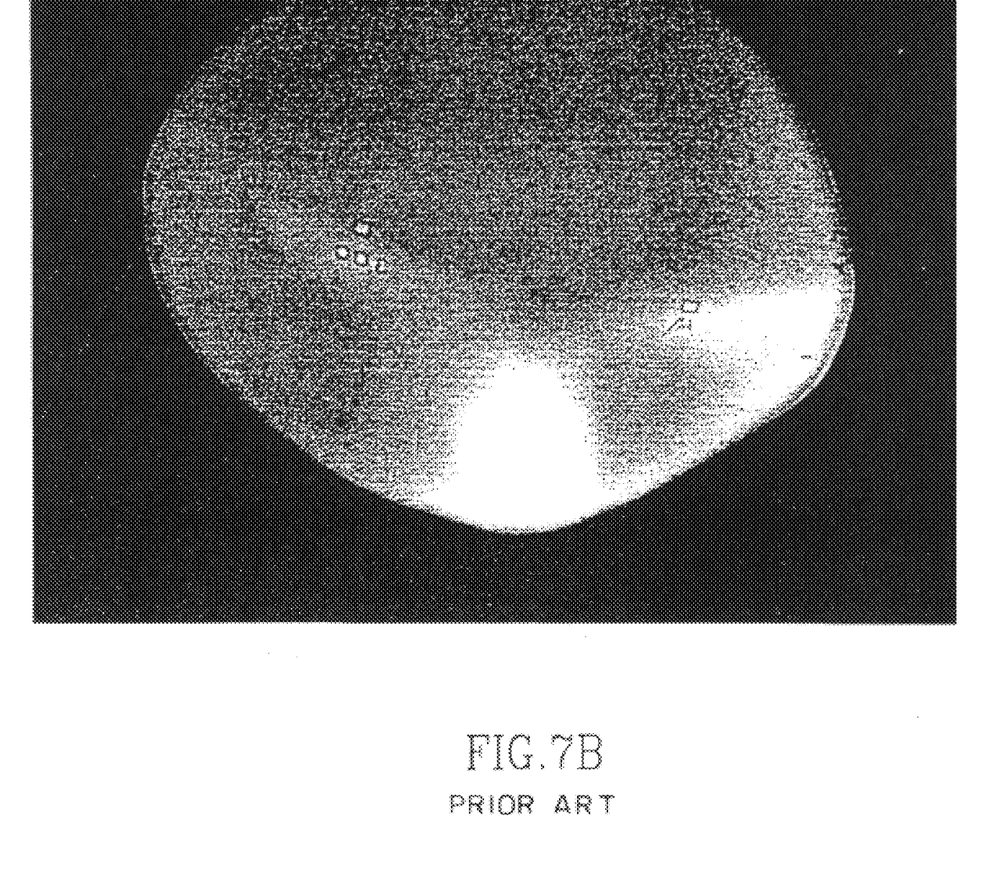
Figure 8A:
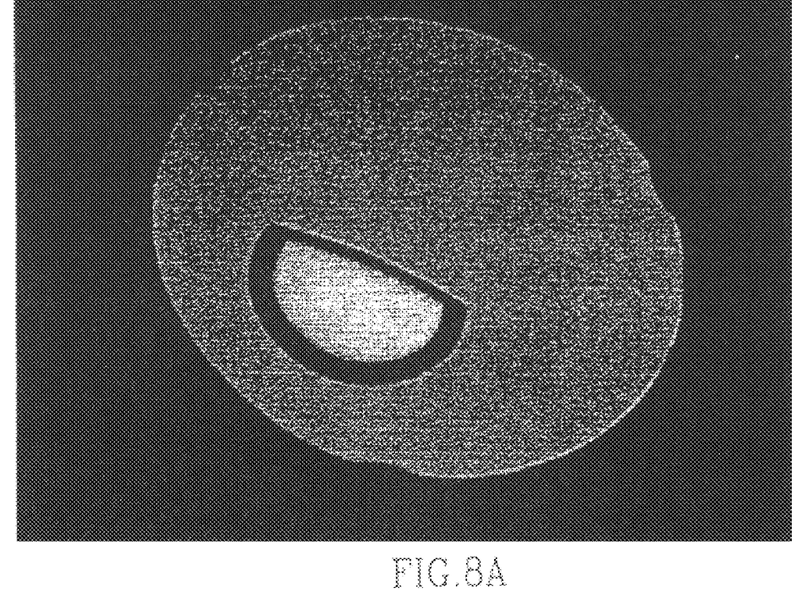
FIGS. 8a and 8b illustrate images of shadow patterns of a bifocal lens with its cylindrical power obtained, respectively, in accordance with the present invention and conventionally.
Figure 8B:
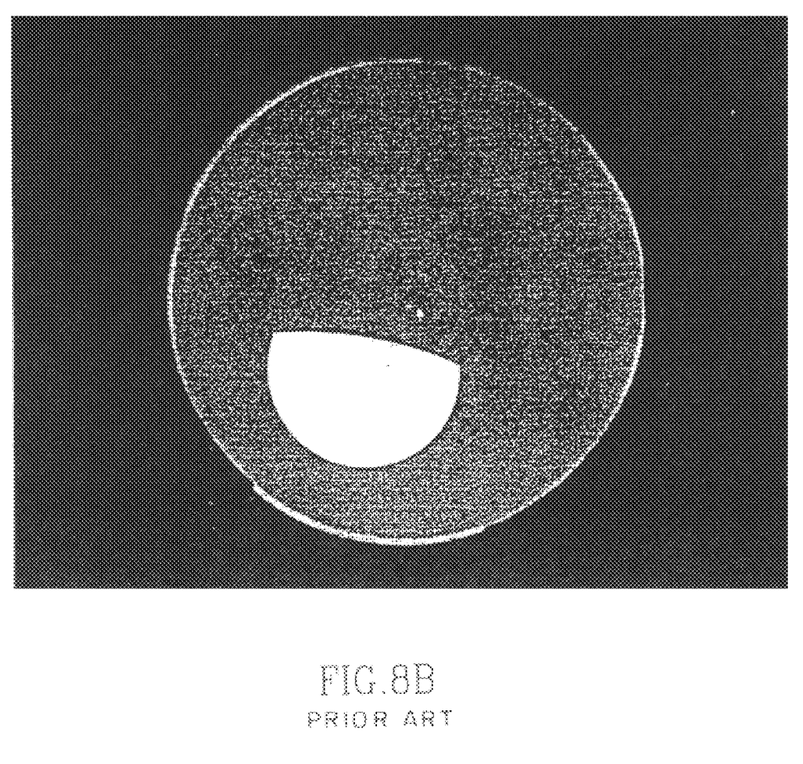

FIGS. 7a and 7b illustrate images of shadow patterns of a progressive lens and FIGS. 8a and 8b illustrate images of shadow patterns of a bifocal lens with its cylindrical power, obtained, respectively, by the method of the present invention and by conventional means. As seen, in the images obtained by the method of the present invention (FIGS. 7a and 8a), the shapes of the lenses as well as the shapes and the disposition of the defects therein are seen undistorted if compared with those obtained by conventional means (FIGS. 7b and 8b).

The method of the present invention and the apparatus may have features which may differ, within the scope of the invention, from the features described above and shown in the drawings.

I claim:

1. A method for the inspection of an optical object for the existence therein of inhomogeneities, said method comprising
    providing a beam of inspection radiation and directing said beam on said optical object so that each point thereof is illuminated at a single respective angle;
    projecting said beam through said optical object on a projection screen and obtaining thereby a shadow pattern thereof, said optical inhomogeneities being distinguishable in said shadow pattern owing to a difference in the brightness of the areas corresponding thereto over the background brightness of the pattern;
    imaging said shadow pattern through said optical object in such a manner that the rays forming said image pass through each point of the optical object at an angle corresponding to said angle at which said point is illuminated; and
    detecting and analyzing said image of the shadow pattern.

2. A method according to claim 1, wherein optical paths of the rays of said beam of inspection radiation coincide with optical paths of corresponding imaging rays.

3. A method according to claim 2, wherein the beam incident on the inspected optical object is a diverging beam.

4. A method according to claim 2, wherein the beam incident on the inspected optical object is a collimated beam.

5. A method according to claim 2, wherein the beam incident on the inspected optical object is a converging beam.

6. A method according to claim 1, wherein the inspected optical object is a specular element having a reflective surface, said shadow pattern being produced by the radiation reflected from, and imaged via, said reflective surface.

7. A method according to claim 1, wherein said optical object is a linearly translated sheet material illuminated by a stripe of light directed transversely to the direction of translation, the image being detected by a transversely oriented multi-element line detector.

8. A method according to claim 1, used for automated quality control.

9. A method according to claim 1, used for the mapping of optical objects based on the local measurements of optical power thereof.

10. An apparatus for the inspection of an optical object for the existence therein of inhomogeneities comprising:
    illumination means for providing a diverging beam of inspection radiation and for the illumination of said optical object thereby so that each point thereof is illuminated at a single angle of the incident radiation, and providing, by means of said optical object, a shadow pattern thereof on a projection screen;
    imaging means for imaging said shadow pattern through said optical object in such a manner that rays forming said image pass through each point of the optical object at said angle at which said point is illuminated; and
    image detecting means and image processing means for analyzing said image of the shadow pattern for said inhomogeneities.

11. An apparatus according to claim 10, wherein an exit pupil of the illumination means and an entrance pupil of said imaging means are optically equidistant from the inspected optical object.

12. An apparatus according to claim 10, wherein said illumination means is a point source of radiation.

13. An apparatus according to claim 10, wherein said illumination means comprises a beam-splitting element.

14. An apparatus according to claim 10, wherein said projecting screen is a high resolution back-scattering surface.

15. An apparatus according to claim 10, wherein said image detecting means is a multi-element detector capable of measuring the brightness distribution in the image of the shadow pattern.

16. An apparatus according to claim 10, further comprising optical elements for the correction of the form of said shadow pattern.

17. An apparatus according to claim 10, wherein said optical object is a linearly translated sheet material, said illumination means being capable of illuminating said material with a stripe of radiation oriented transversely to the direction of translation, and said image detecting means is a multi-element line detector.

18. An apparatus according to claim 11, wherein said illumination means is a point source of radiation.

19. An apparatus according to claim 18, wherein said projecting screen is a high resolution back-scattering surface.

20. An apparatus according to claim 19, wherein said image detecting means is a multi-element detector capable of measuring the brightness distribution in the image of the shadow pattern.

\* \* \* \* \*